(12) United States Patent
Vergassola et al.

(10) Patent No.: US 7,885,768 B2
(45) Date of Patent: Feb. 8, 2011

(54) METHOD AND SYSTEMS FOR LOCATING A SOURCE OF PARTICLE, MOLECULE, OR FRAGMENT OF MOLECULE USING THEIR RECEPTION RATE

(75) Inventors: Massimo Vergassola, Paris (FR); Boris Shraiman, Goleta, CA (US); Emmanuel Villermaux, Marseilles (FR)

(73) Assignee: The Regents of the University of California, Oakland, CA (US)

( * ) Notice: Subject to any disclaimer, the term of this patent is extended or adjusted under 35 U.S.C. 154(b) by 783 days.

(21) Appl. No.: 11/481,944

(22) Filed: Jul. 7, 2006

(65) Prior Publication Data

US 2008/0010023 A1 Jan. 10, 2008

(51) Int. Cl.
G06F 7/00 (2006.01)

(52) U.S. Cl. ............................. 702/19; 702/20; 702/22; 702/30; 702/33; 702/94; 703/11; 703/12

(58) Field of Classification Search ........................ None
See application file for complete search history.

(56) References Cited

U.S. PATENT DOCUMENTS 6,930,596 B2 * 8/2005 Kulesz et al. ............... 340/506

7,477,993 B2 * 1/2009 Sunshine et al. ............. 702/22

OTHER PUBLICATIONS

O'Neill (Dissertation Abstracts International, (2002) vol. 63, No. 7B, p. 3395). in four parts.*

* cited by examiner

*Primary Examiner*—Mary K Zeman
(74) *Attorney, Agent, or Firm*—Oblon, Spivak, McClelland, Maier & Neustadt, L.L.P.

(57) ABSTRACT

A method and systems for locating a source of particles, molecules, or fragments of molecules using particle, molecule, or fragment of molecule reception rate is disclosed. According to the invention, the particle, molecule, or fragment of molecules diffusion parameters in the search space are determined and a lattice is designed on the search space. After having determined whether or not at least one particle, molecule, or fragment of molecule is detected by a sensor, a probability is computed for each node of said search space lattice. The probability associated to each node of the search space lattice corresponds to the probability that the particle, molecule, or fragment of molecule source is located on the node. Then, the move of the sensor is evaluated according to the entropy of the computed probabilities.

14 Claims, 7 Drawing Sheets

Fig. 6a
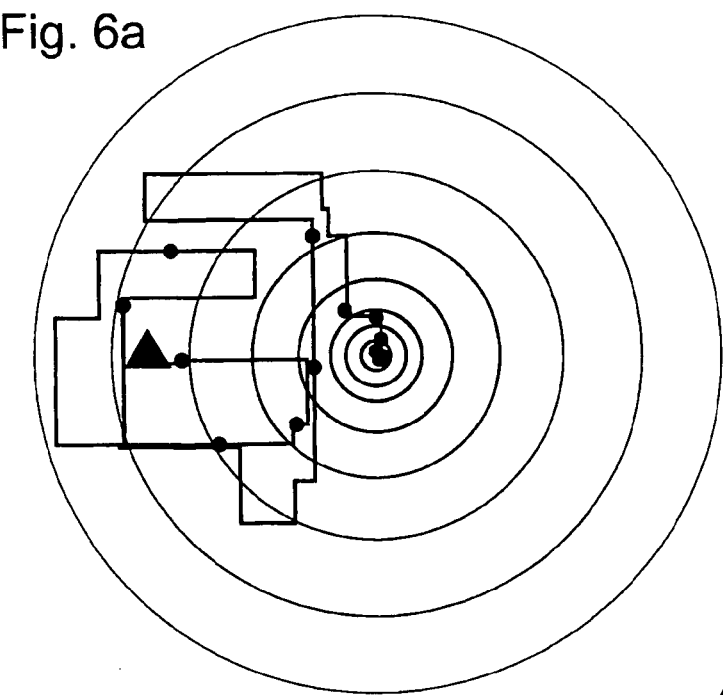
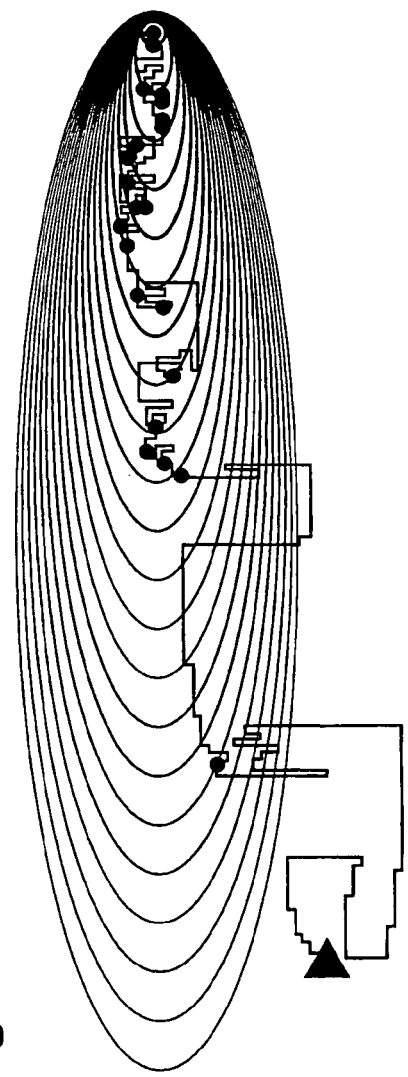
Fig. 6b

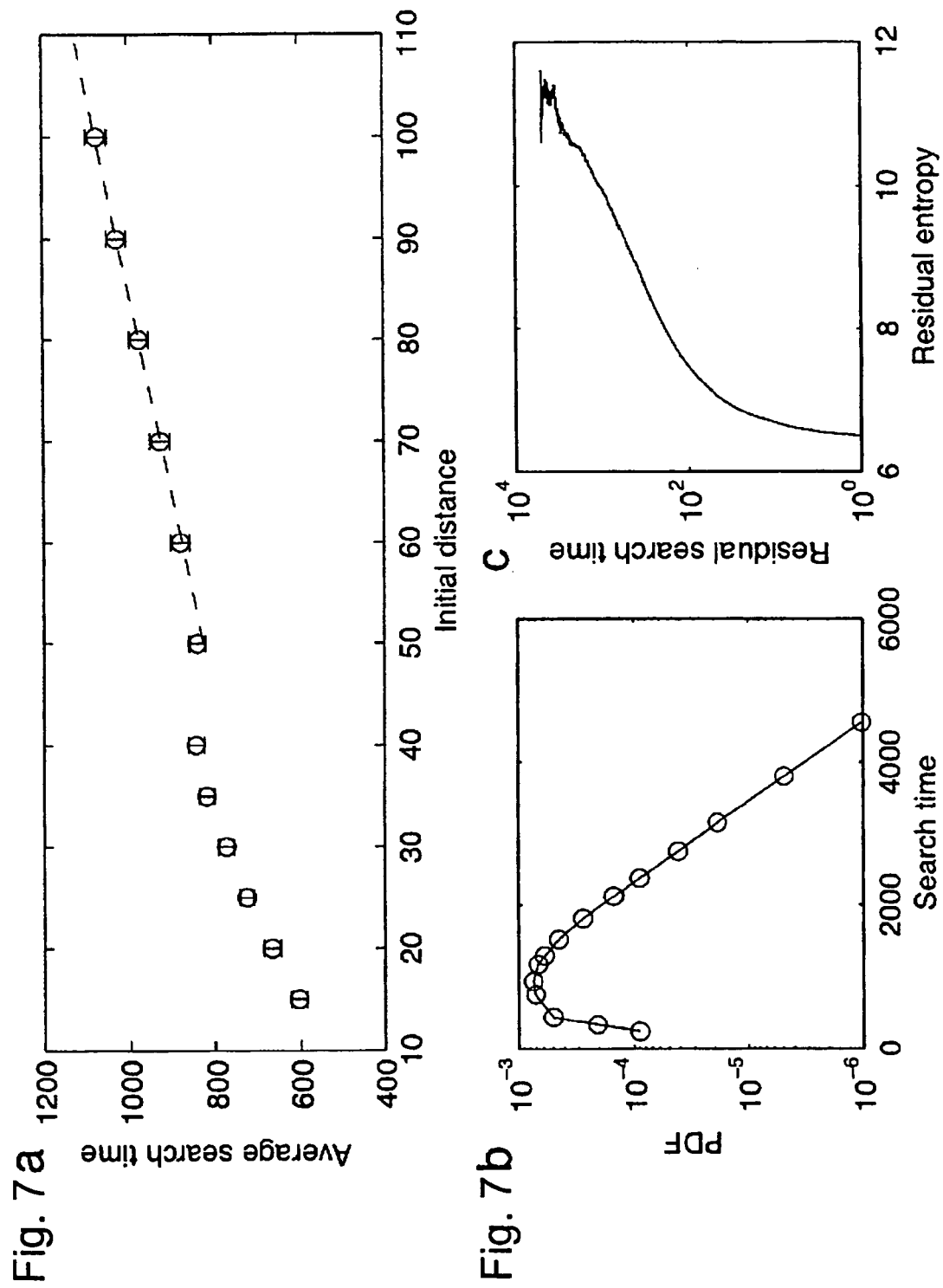

METHOD AND SYSTEMS FOR LOCATING A SOURCE OF PARTICLE, MOLECULE, OR FRAGMENT OF MOLECULE USING THEIR RECEPTION RATE

FIELD OF THE INVENTION

The present invention relates generally to a method and systems for locating particle or molecule sources and more specifically to a method and systems for locating the source of diffused particles or molecules using their reception rate.

BACKGROUND OF THE INVENTION

Even if locating particle sources like odorous substances is a common task for animals, for example when searching for food, machines face difficulties in handling such problem despite the needs e.g., locating drugs, chemical leaks, explosive, and mines. Semiconductor gas-sensors are able to detect the presence or not of specific odorous substances and to determine their concentration however, locating the sources has to take into account the environment and particularly the air or liquid flow in which the odorous substance diffuses in a chaotic way.

Chemotactic bacteria lack a sense of position and their motion is perturbed by thermal noise, yet guided by the local gradient in nutrient concentration they can find its source. Macroscopic searchers endowed with a sense of direction and position often face a different problem: lack of local clues pointing towards the location of the target. For example, animals sensing odors in air or water detect them only intermittently as patches of odor sweep by, carried by winds and currents. Because of randomness of the advection and mixing process, local gradients of odor intensity do not point to the source and the searcher must devise a strategy of movement based upon sporadic cues and partial information.

Like chemotactic bacteria, most of the robots equipped with odor sensor use the local concentration gradient of an odorous substance to determine locally the direction of its source, referred to as chemotactic search strategy. However, chemotactic search strategies based on local concentration gradients require concentration to be sufficiently high so that its average difference measured at two nearby locations is larger than typical fluctuations. The signal-to-noise ratio depends of course on the averaging time and might be improved by waiting. However, average concentration may be decaying rapidly e.g., exponentially, with the distance away from the source and in this weak signal-to-noise (dilute) case waiting becomes worse than exploratory motion. As an illustration, FIG. 1 depicts an example of an environment where odorous substance is diffused within the atmosphere and where odorous substance concentration can not be used locally to determine the odorous substance source.

Chemotaxis requires a reliable measurement of local gradients. This is not feasible for robots located far away from the source and severely limits the range of application of automated source localization by robots. Existing chemocatic robots might take several minutes to locate a few meters away.

Therefore, there is a need to provide a method and systems for solving the challenge of searching particle or molecule sources in dilute environment e.g., for the design of sniffers or robots that track chemicals emitted by drugs, chemical leaks, explosives and mines.

SUMMARY OF THE INVENTION

Thus, it is a broad object of the invention to remedy the shortcomings of the prior art as described here above.

It is another object of the present invention to provide a method and systems for locating a particle or molecule source in diffuse environment.

It is another object of the invention to provide a method and systems for locating a particle or molecule source using particle or molecule reception rate.

It is still another object of the invention to provide a method and systems for locating a particle or molecule source by determining the probability for each point of the search space to be the particle or molecule source and by continuously updating these probabilities.

It is still another object of the invention to provide a method and systems for determining the direction of a particle or molecule source using the entropy of the probability of each search space point to be the particle or molecule source.

It is a particular object of the invention to provide a method and systems for determining the location of a particle or molecule source using the entropy of the probability of each search space point to be the particle or molecule source.

The accomplishment of these and other related objects is achieved by a method for locating a source of particles, molecules, or fragments of molecules in a search space using a mobile sensor adapted to detect the presence of such particle, molecule, or fragment of particle, the method comprising the steps of, determining the particle, molecule, or fragment of molecule diffusion parameters in the search space;
designing a lattice on the search space;
determining if at least one particle, molecule, or fragment of molecule is detected by the sensor;
computing a probability for each node of the search space lattice to be the source of the particles, molecules, or fragments of molecules according to the determined particle, molecule, or fragment of molecule diffusion parameters and to the detected particles, molecules, or fragments of molecules;
evaluating a movement of the sensor according to the computed probabilities.

Further embodiments of the invention are provided in the appended dependent claims.

Further advantages of the present invention will become apparent to the ones skilled in the art upon examination of the drawings and detailed description. It is intended that any additional advantages be incorporated herein.

BRIEF DESCRIPTION OF THE DRAWINGS

FIG. 6, comprising FIGS. 6a and 6b, presents the result of a numerical simulation of particle source localization, in the absence of wind and in the presence of wind, respectively.

FIG. 7 depicts the quantitative characterization of search algorithm according to the invention.

DETAILED DESCRIPTION OF THE PREFERRED EMBODIMENTS

An example of organisms performing olfactory search in a dilute limit is provided by moths which use pheromones to locate their mates. Moths are known to proceed upwind via counterturning patterns of extended ("casting") or limited ("zigzagging") crosswind width thought to correlate with low and high rates of odor detection. In the dilute limit the searcher detects odor in a sporadic sequence of distinct events arising from its encounters with patches of fluid (or air) where turbulent mixing has failed to dissipate the advected odor down to the level below detectability threshold. These detection events, or "hits", are separated by wide "voids" with no detectible signal. Because the probability of odor encounter depends on the distance from the source, the set of encounters which occurred at times $\{t_i\}$ along the search trajectory r(t) carries information about the source location.

According to the invention there is provided a method and systems based upon the rate of acquisition of information on particle or molecule source location, as estimated by the searcher, wherein the strategy of motion maximizes the expected rate of information gain. By particle or molecule source, one should understand any types of particles or molecules, comprising biological molecules such as protein or protein fragments, particularly pathogens. The efficiency of the method and system in reaching the source has been demonstrated and quantified computationally using a model of odor plume propagation as well as experimental data on mixing flows. An example of application the search algorithm is relevant to is the design of olfactory robots with applications to detection of chemical leaks and explosives however, the method of the invention can be applied more broadly in the context of searching with sparse information and provides a framework for quantitative understanding of the balance between the competing "exploration" and "exploitation" behaviors in learning processes.

For sake of illustration, the following description concerns a robot searching for an odorous substance source. By robot, one should understand a system comprising, a detector of particles or molecules (of the type emitted by the source to be localized);
a system allowing its mobility; and,
a processor to implement the calculations called by the decision protocol.

If detection in the presence of wind is foreseen, an anemometer to detect the mean direction of winds and/or currents is preferably embedded within the robot or, alternatively, the wind characteristics are transmitted to the robot.

Figure 1:
FIG. 1 illustrates an example of an environment where odorous substance is diffused within the atmosphere and where odorous substance concentration can not be used locally to determine the odorous substance source.
Figure 2:
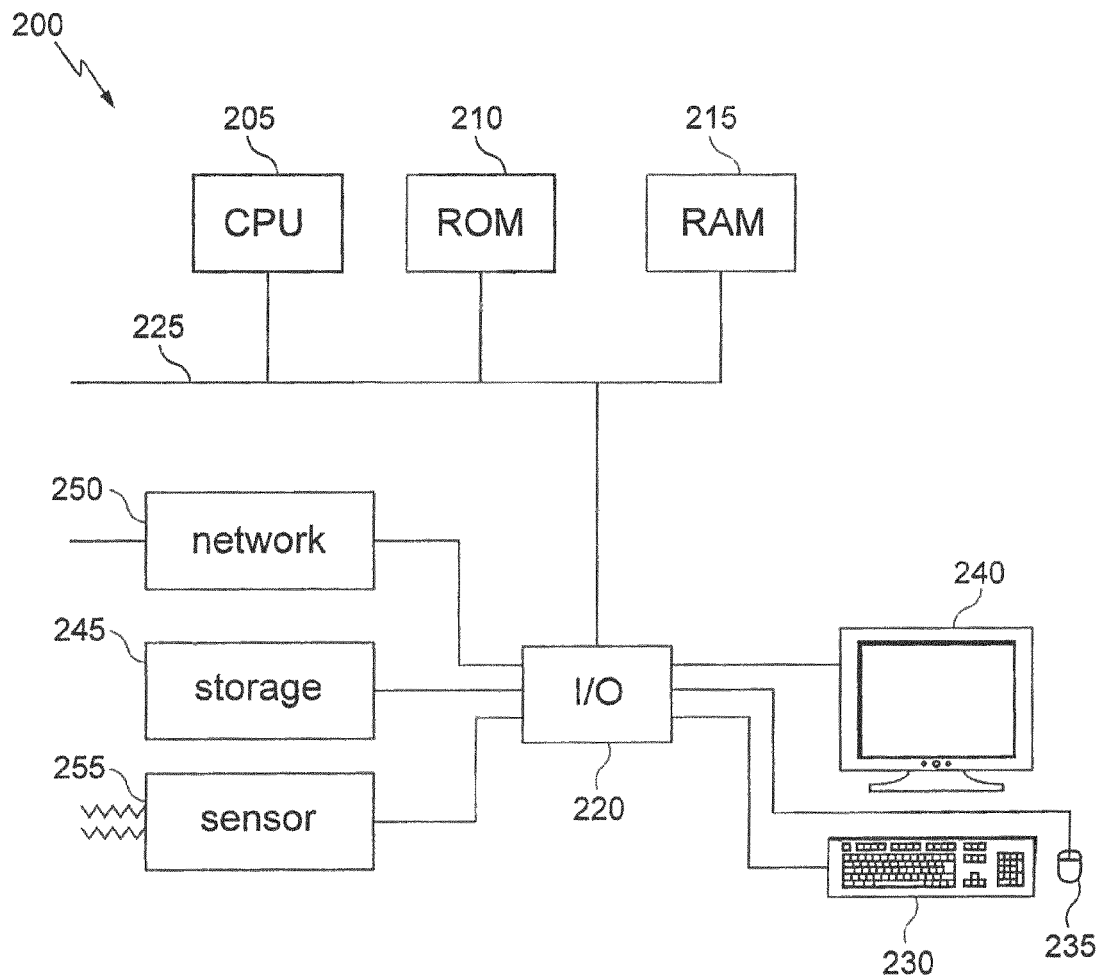
FIG. 2 shows an example of a computer architecture adapted to implement the method of the invention.

In a specific embodiment, the method of the invention is implemented within a standard computer architecture embedded within the robot. FIG. 2 shows an example of a computer architecture adapted to implement the method of the invention. FIG. 2 illustrates a block diagram of a generic computer device, handheld device, or any kind of computer device, generally referred to as computer 200, in which the present invention can be implemented. The system has a central processing unit (CPU) 205, a Read-Only Memory (ROM) 210, a Random Access Memory (RAM) 215, and an I/O subsystem 220, all of them being connected to a system bus 225. The I/O subsystem 220 may include one or more controllers for input/output devices such as keyboard 230, cursor control device 235, display device 240, mass storage device 245, and network interface 250. Depending upon the application of the system 200, one or more further I/O devices may be connected to the I/O subsystem 220. Typically, the hardware system 200 is controlled by an operating system that can be stored in ROM 210 or in mass storage device 245, which in turn controls various tools and applications that are generally loaded in RAM 215. At least one sensor 255 is connected to the I/O subsystem 220 for detecting the particle or molecule that source is searched. The system may include further sensors to detect other type of particles or molecules, or to analyze the environment e.g., detecting obstacles.

Alternatively, a robot comprising a particle or molecule sensor can be connected to a second computer or server using a wire or a wireless connection so that all the complex computation tasks can be done by the second computer or server. In such case, the computer embedded within the robot is used to control the robot, to transmit information relative to detected particles or molecules to the computer or server, and to receive instructions from the second computer or server concerning robot movement.

Example of Algorithm According to the Invention

The method of the invention is based upon the evaluation of the probability, for each point of the searching space, to be the particle or molecule source. Knowing such probability field, each possible movement of the robot is analyzed so as to maximize the diminution of the probability field entropy. To that end, the search space is divided into sub-spaces according to a predetermined grid where the probability is estimated for each node.

Figure 3:
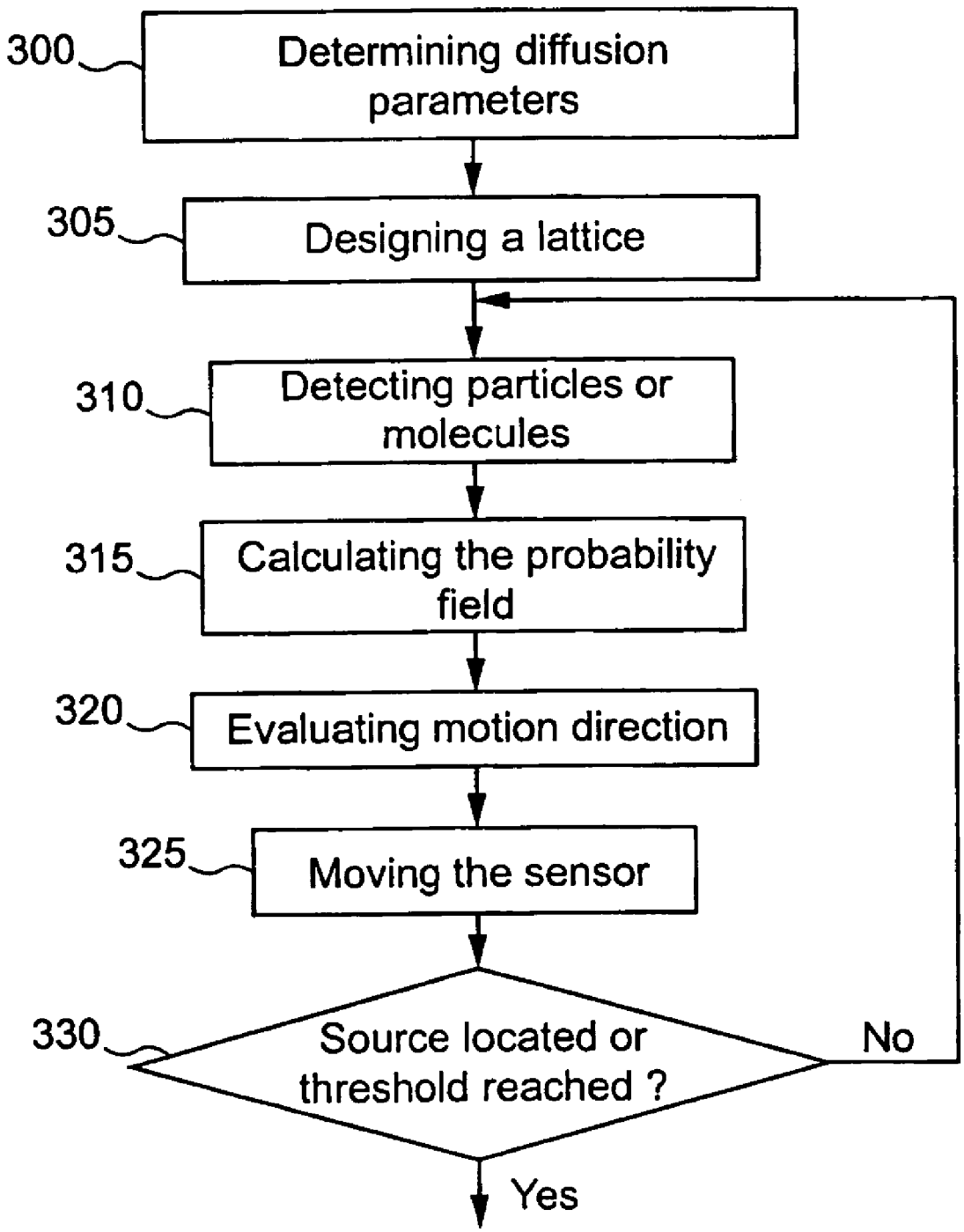
FIG. 3 depicts the main steps of the algorithm according to the invention.

The main steps of the algorithm according to the invention are depicted on FIG. 3 and consists in, determining the particle or molecule diffusion parameters in the search space (step 300);
designing a lattice on the search space (step 305);
detecting in the search space, with or without wind or current, of one or several types of particles or molecules characteristic of the source to be localized, using detectors or sensors, preferably carried by a robot (step 310);
calculating a probability field for the location of the source on the basis of the history of detections i.e., updating the probability for each node of the search space lattice to be the particle or molecule source, using the particle or molecule diffusion parameters (step 315);
evaluating the direction of motion of the detector or sensor, or of the robot carrying the sensor, (step 320). The extension of the region of space where the source has a sizable chance of being located is estimated according to the probability distribution constructed at the previous step. The choice of the direction of motion is then dictated by the principle that the extension of the region (and thus the uncertainty on the location of the source) should reduce as rapidly as possible. This is quantified by the reduction of probability field entropy;
moving the robot, or at least the detectors or sensors according to the direction of motion evaluated in the previous step (step 325); and,
repeating the last four steps until the particle source is located or until a predetermined parameter reaches a predetermined threshold (step 330).

As mentioned above, one of the advantages of the algorithm according to the invention, as compared to most of the existing chemotactic strategies, is related to its capacity to deal with an uncertain environment where gradients cannot be reliably measured. No wind or particular reference points and/or directions are needed for the rapid location of the source even if they might be exploited if available. Note also that if several types of particles or molecules are detectable and characteristic of the spectrum of emission of the source, they can be combined according to the information that they provide about the location of the source. The process of source location will consequently be sped up.

Determination of the Particle or Molecule Diffusion Parameters

The rate of encounters between a spherical particle or molecule of radius a and particles or molecules diffusing with effective diffusivity D is given by the following classical Smoluchowski's expression, $$J(r) = 4\pi Dac(r) \qquad (1)$$

where $c(r)$ is the concentration of particles or molecules at position r, formally r(t) (for sake of clarity, the time index is not systemically written).

For a reliable assessment of concentration, one collects local detection events over time $T_{int}$. The average number of detection events will then be $J(r)T_{int}$. Typical fluctuations are of the order of the square root of the mean. The condition for the signal to emerge out of the noise reads then, $$\sqrt{T_{int} Dac(r)} \gg 1 \qquad (2)$$

Reliable measurements of concentration gradients require the difference in counts across the interval of measurement to be above the noise level. The corresponding conditions read, $$\left(vT_{int}\frac{dc}{dr}\right)T_{int}Da \gg \sqrt{DcT_{int}a} \; ; \qquad (3)$$

$$vT_{int}\frac{d\log c}{dr} \ll 1$$

Here, v is the velocity of the searcher and dc/dr is the concentration gradient. The first inequality in the previous relation gives the condition that the signal-to-noise ratio for the difference in the number of hits experienced by the searcher across the integration time $T_{int}$ be larger than unity. The second inequality is the requirement of locality, i.e. that the change in concentration across the distance spanned during $T_{int}$ be small compared to the concentration itself. Assuming an exponentially decaying concentration $\exp(-r/\lambda)$, reliable integration time $T_{int}$ scales as $\exp(r/3\lambda)$ where $\lambda$ represents the typical length traveled by particles or molecules away from the source.

A first reasonable statistics of odor encounters in a turbulent flow is provided by a model where detectable particles are emitted by the source at rate R, have a finite lifetime $\tau$, propagate with isotropic effective diffusivity D and are advected by a mean current or wind V. It should be understood that other propagation models can be used, there are no particular restrictions on their nature.

The field of mean stationary concentration $c(r|r_0)$ generated at position r by a source located at position $r_0$, will satisfy the following advection-diffusion equation, $$0 = V\nabla_y c(r|r_0) + V\Delta c(r|r_0) - \frac{1}{\tau}(r|r_0) + R\delta(r_0) \qquad (4)$$

where the wind has been taken to blow in the negative y-direction, $\delta(r_0)$ representing the source term. One should notice that V is the mean velocity and that the instantaneous velocity fluctuates both in direction and amplitude due to the noise term described by the effective diffusivity term D characterizing the sum of both the turbulent diffusivity and the (usually much smaller) particle or molecular diffusivity. Both in two and three dimensions, equation (4) admits an analytical solution. In 2D, the solution reads as follow, $$c(r|r_0) = \frac{R}{2\pi D} e^{-\frac{(y-y_0)V}{2D}} K_0\left(\frac{|r-r_0|}{\lambda}\right) \qquad (5)$$

wherein $(y-y_0)$ represents where the wind was taken to blow in the y direction, $y_0$ is the y-coordinate of the source, and wherein, $$\lambda = \sqrt{\frac{D\tau}{1 + \frac{V^2\tau}{4D}}} \qquad (6)$$

$K_0$ being the modified Bessel function of order zero. A similar expression is derived in three dimensions as:

$$c(r|r_0) = \frac{R}{4\pi Dr} e^{-\frac{(y-y_0)V}{2D}} e^{-\frac{r}{\lambda}} \qquad (7)$$

where $\lambda$ is given by the relation 6.

A spherical object of small linear size a moving into such media will experience a series of encounters at rates $R(r|r_0)$ given by the Smoluchowski's arguments. In three dimensions, the expression derives from relations 1 and 7.

In two dimensions, the time of return to a given location for a diffusive particle is known to have a logarithmic divergence. The logarithmic divergence is regularized by the presence of a finite lifetime of detected particles so that relation 1 takes the following form, $$R(r|r_0) = \frac{2\pi Dc(r|r_0)}{\ln\left(\frac{\lambda}{a}\right)} = \frac{R}{\ln\left(\frac{\lambda}{a}\right)} e^{\frac{(y_0-y)V}{2D}} K_0\left(\frac{|r-r_0|}{\lambda}\right) \qquad (8)$$

with the concentration profile given by relation 7, where $R(r|r_0)$ represents the rate at which particles or molecules are received at point r from particle or molecule source located in $r_0$.

As a consequence, in three dimensions, the rate at which particles are received at point r from particle source located in $r_0$ can be expressed as follow, $$R(r|r_0) = \frac{aR}{|r-r_0|} e^{-\frac{(r-r_0)}{\lambda}} e^{\frac{(y_0-y)V}{2D}} \qquad (9)$$

The properties of propagation of the cues through the medium and their frequency of emission have hitherto been considered as known. Robots designed to detect patches of odors—sniffers—are typically endowed with sensors measuring the time-trace of the wind that provide them with relatively reliable estimates of mean quantities such as the mean wind and the Root Mean Square (RMS) $V_{rms}$ of velocity fluctuations. The sporadic nature of the signal detected by sniffers comes from the fact that odors are typically transported by strongly turbulent fields that efficiently mix and make the patches spread out and decay in intensity with time.

Parameters of turbulent flows are notoriously hard to estimate but the major advantage here is that searches according to the invention are not maximum likelihood strategies and are more robust to errors and incomplete information. Sophisticated modelling of the turbulent medium is therefore not crucial (and it is hard to imagine that birds and moths rely on fine-tuning of parameters in their searches). The most effective approach to parameter estimation for the case of sniffers appears to be the following. In the absence of a precise value of the parameters of the medium, one can start searches with rough estimates which ensure that the rate function $R(r|r_0)$ is shallower than in reality. The purpose is that, in the absence of precise information, broad estimators of the rate function will avoid wrong estimates that could drive the searcher astray e.g., to the boundaries of the search space where the search is taking place. The searcher will thus typically arrive to the source, albeit in times much longer than with the correct estimation of $R(r|r_0)$. Once arrived to the source, and thus knowing the source position $r_0$, the searcher can use the trace T of detections along its trajectory to estimate the parameters of the medium and the source.

For example, let us consider the problem of learning parameters for the model described previously. Suppose that the mean velocity V is accessible via the sensors and, just for the sake of the argument, that the turbulent diffusivity D, the RMS velocity fluctuations $V_{rms}$ and the particle lifetime $\tau$ are related as $D=V_{rms}^2\tau$. This is a classical dimensional estimate of turbulent diffusivity and reduces the space of parameters to two variables so that one can visualize the likelihood surface. One shall take the rate of emission of the source R and the effective diffusivity D as independent variables and try to learn the parameters of a medium having unit values for D, R and V and a turbulence level $V_{rms}/V=20\%$, a typical value in turbulent jets. Choosing a shallow rate function $R(r|r_0)$ as initial guess corresponds to safe overestimates of D and 1/R e.g., by two orders of magnitude $D_{est}=1/R_{est}=100$. Starting the searcher with these very rough estimates and from initial distances 50 i.e., twice the advection length $V\tau=25$, slows down the search by about a factor 7. Still, more than half of the searches arrive to the source without ever touching the boundaries of the search space. The minimum is clearly located at the real values D=R=1 and the convexity of the curve makes it easy to find it by any standard minimization algorithms, such as simplex method, simulated annealing or conjugate gradient.

Estimation of the Posterior Probability Distribution

In the following description, $\tau_t$ denotes times and coordinates of the "hits" i.e., the points of the robot trace where sensors have been activated. The trace $\tau_t$ might be thought of as a message, sent by the particle or molecule source and transmitted to the searcher with strong noise due to the random nature of particle or molecule propagation in the turbulent medium. Decoding of the message is implemented using Bayes formula to construct, given the received signal, the posterior probability distribution $P_t(r_0)$ for the unknown location of the source $r_0$. The trace $\tau_t$ and the posterior probability distribution $P_t(r_0)$ are dynamical objects, continuously updated with time. The specific decoding protocol depends of course on the nature of the detection events and the transmitting medium. For sake of illustration, the evaluation of the probability distribution $P_t(r_0)$ is based upon the particle or molecule diffusion model discussed above.

The probability distribution posterior to experiencing a trace $\tau_t$ of uncorrelated odor encounters can be expressed as follow, $$P_t(r_0) = \frac{\zeta_{r_0}(\tau_t)}{\int \zeta_x(\tau_t)dx} = \frac{\exp\left[-\int_0^t R(r(t')|r_0)dt'\right]\prod_{i=1}^H R(r(t_i)|r_0)}{\int \exp[-\int_0^t R(r(t')|x)dt']\prod_{i=1}^H R(r(t_i)|x)dx} \quad (10)$$

where, H is the number of hits along the trajectory, the $t_i$'s are the corresponding times and $\zeta_{r_0}(\tau_t)$ is the likelihood to observe the trace $\tau_t$ of odor encounters for a source located at $r_0$. This expression is supplemented by the prescription that visited regions where the source was not found have zero probability. Note that $P_{t+\Delta t}(r_0)$ factorizes as $P_t(r_0)$ times a term that depends on the hits received in the $\Delta t$ interval. Thus, keeping track of the whole trajectory and history of detections is not required. The expression for $P_t(r_0)$ is derived by taking the probability of a "hit" during an infinitesimal interval dt to be $R(r|r_0)dt$ and the probability of not being hit to be $\exp[-R(r|r_0)dt]$.

There are obvious quantitative improvements one could obtain by accounting for correlations in the detections within coherent plumes. Detailed models of plumes have already been discussed in the literature and thus, a brief discussion of a simple way to account for time-correlations in the detections is presented here. The model is based on the following likelihood of experiencing a trace $\tau_t$ of correlated odor encounters, $$\zeta_{r_0}(\tau_t) = \\ e^{-\sum_i\left[\int_{V_i} R(r(t')|r_0)dt' + \int_{D_i} Q(r(t')|r_0)dt'\right]}\prod_{i=1}^H R(r(t_i)|r_0)\prod_{j=1}^{H'} Q(r(t_j)|r_0) \quad (11)$$

wherein, the $V_i$'s ($D_i$'s) are the time intervals of absence (presence) of detections, H and the $t_i$'s are the number and times of transition from no-detection to detection intervals ($V_i \rightarrow D_i$) and, finally, H' and t'i are the number and times of the opposite transitions, from detection to no-detection. The function $Q(r(t_j)|r_0)$ controls the extension of patches of particles or molecules as a function of the distance to the source $r_0$. The posterior probability distribution $P_t(r_0)$ is constructed as done previously, by using the Bayes formula, $$P_t(r_0) = \frac{\xi_{r_0}(\tau_t)}{\int \xi_x(\tau_t)dx} \quad (12)$$

The following expression amounts to assuming that patches of odors have finite extensions and thus, the searcher will spend finite amounts of time within them. As mentioned above, the extension of patches as a function of the distance to the source is controlled by the function $Q(r|r_0)$. In the simplest possible setting where the function $Q(r|r_0)$ is taken to be constant in space, the expression for the posterior probability distribution simplifies as, $$P_t(r_0) = \frac{\exp\left[-\sum_i \int_{V_y} R(r(t') | r_0) dt'\right] \prod_{i=1}^{H} R(r(t_i) | r_0)}{\int \exp\left[-\sum_i \int_{V_y} R(r(t') | x) dt'\right] \prod_{i=1}^{H} R(r(t_i) | x) dx} \quad (13)$$

The same structure as for independent hits is obtained but consecutive detections are not overcounted. One should notice that there are no additional parameters to be estimated. Variations along the same lines might be considered by introducing additional parameters, for example treating the time distance to a previous hit in a patch as a free parameter and estimating it from the data.

Figure 4:
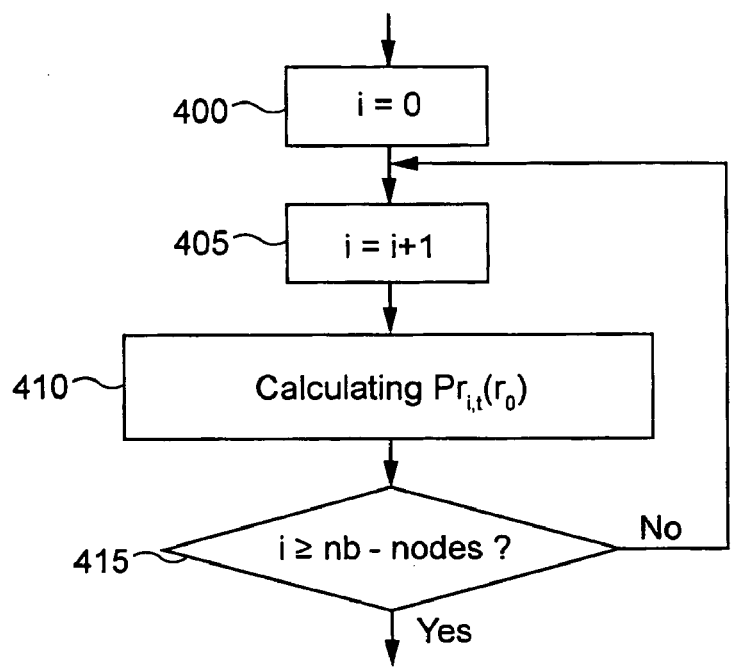
FIG. 4 depicts the main steps of evaluating the posterior probability of each node of the search space lattice.

FIG. 4 depicts the main steps of evaluating the posterior probability of each node of the search space lattice, corresponding to box 315 of FIG. 3. As illustrated, a variable i representing the index of a node of the searched space lattice among all the nodes is set to zero (step 400) and incremented by one (step 405). The probability $P_{r_i,t}(r_0)$ that node $r_i$ corresponds to the source $r_0$ is calculated according to relation 10 or to relation 13 (step 410) and a test is performed to determine whether or not the probability of each node of the search space lattice has been evaluated at time t (step 415). If the probability of all the nodes of the search space lattice have not been evaluated at time t the last three steps i.e., steps 405 to 415, are repeated.

Determination of the Sensor Movement

Given a probability distribution $P(r_0)$ for the location of the source, the Shannon's entropy S for the distribution can be expressed as, $$S \equiv -\int dx P(x) \ln P(x) \quad (14)$$

The entropy quantifies how spread-out the distribution is and goes to zero when the position of the source is localized to one site i.e., is known. The rate of acquisition of information is quantified by the entropy rate of reduction. The main problem for the searcher is that the real probability distribution is unknown (to it) and must be estimated from the available data i.e., the history of its odor encounters. As information accumulates, the entropy of the estimated distribution decreases and with it the expected time to locate the source. The searcher is faced with conflicting choices of either proceeding with its current information i.e., going to the estimated most probable source location, or alternatively, pausing to gather more information and obtain a more reliable estimate of the source distribution. The problem of dealing with only partially reliable information is quite general and has received a systematic formulation in learning theory in terms of the "exploration versus exploitation tradeoff" to be struck for effective learning. In the search context, "exploitation" of the currently estimated $P_t(r_0)$ by chasing locations of maximal estimated probability is very risky because it can lead off the track. The most conservative "exploration" approach is to accumulate information before taking any step. This strategy is safe but not productive and is inferior to more active exploration, e.g. systematic search in a particular sector.

According to the present invention, the searcher chooses, at each time step, the direction which locally maximizes the expected rate of information acquisition, to balance exploration and exploitation. Specifically, the searcher chooses, among the neighbouring nodes of the lattice and standing still, the movement which maximizes the expected reduction in entropy of the posterior probability field. Expectations are based on the information currently available i.e., the field $P_t(r_0)$ itself. Entropy decreases (and thus information accumulates) faster close to the source because cues arrive at a higher rate, hence tracking maximum rate of information acquisition will guide to the source much like concentration gradients in chemotaxis.

Supposing that the searcher has arrived at r at time t and gathered information is stored into the field $P_t(r_0)$ having entropy S, the variation of entropy expected upon moving to one of the neighbouring nodes $r_j$ (or standing still) is expressed as, $$\overline{\Delta S}(r \to r_j) = -SP_t(r_j) + (1 - P_t(r_j))[\rho_0(r_j)\Delta S_0 + \rho_1(r_j)\Delta S_1 + \ldots + \rho_n(r_n)\Delta S_n] \quad (15)$$

The first term on the right-hand side corresponds to finding the source i.e., $P_{t+1}$ becoming a $\delta$-function and entropy becoming zero, which occurs with estimated probability $P_t(r_j)$. The second term corresponds to the alternative case when the source is not found at $r_j$. Symbols $\rho_k(r_j)$ denote the probability that k detections be made at $r_j$ during a time step $\Delta t$, given, for independent detections, by a Poisson law, $$\rho_k \equiv \frac{h^k e^{-h}}{k!} \quad (16)$$

The expected number of hits is estimated as $h(r_j)$, where, $$h(r_j) \equiv \Delta t \int P_t(r_0) R(r_j | r_0) dr_0 \quad (17)$$

with $R(r|r_0)$ denoting the mean rate of hits at position r if the source is located in $r_0$, as mentioned above.

The symbols $\Delta S_k$ denote the change of entropy between the fields $P_{t+1}(r_0)$ and $P_t(r_0)$. As derivable from relation (15), two effects contribute to $\Delta S_k$, $P_{t+1}(r_j) \equiv 0$ since the source was not found; and, the estimated posterior probabilities are modified by the k cues received.

The first term in is the exploitative term, weighing only the event that the source is found at the point $r_j$ and favouring motion to maximum likelihood points. The second contribution is the information gain from receiving additional cues. It appears even when the searcher does not move and thus represents conservative "exploration". Thus, it is observable that the algorithm according to the invention naturally combines both exploitative and exploratory strategies.

Figure 5:
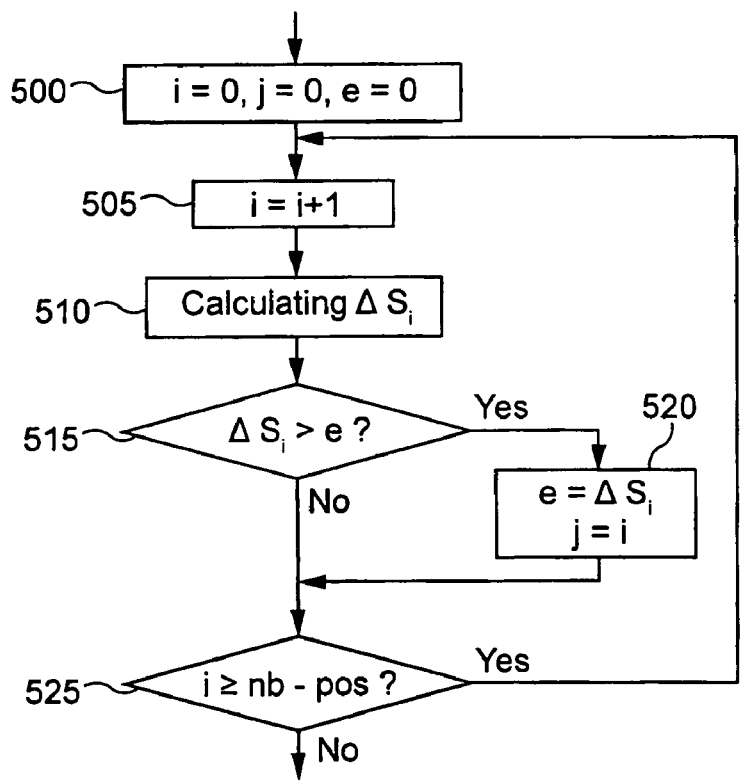
FIG. 5 shows the main steps of evaluating the next optimal movement of the particle or molecule sensor according to the posterior probability of each node of the search space lattice.

Therefore, after having estimated the posterior probabilities of all the nodes of the lattice, the entropy variation of each of the next possible sensor position is evaluated so as to choose the one that maximise the entropy reduction. FIG. 5 shows the main steps of evaluating the next optimal movement of the particle or molecule sensor according to the posterior probability of each node of the search space lattice, corresponding to box 320 of FIG. 3. After variables i, j, and e have been initialized to zero (step 500), variable i, representing the possible moves of the sensor, is incremented by one (step 505). The variation of entropy $\overline{\Delta S}(r \to r_i)$ of the probability field $P(r_0)$ is calculated according to relation 15 (step 510) and a test is performed to determine whether or not the variation of entropy $\overline{\Delta S}(r \to r_i)$ is greater than variable e (step 515). If the variation of entropy $\overline{\Delta S}(r \to r_i)$ is greater than variable e, variable e is set to the value of the variation of entropy $\overline{\Delta S}(r \rightarrow r_i)$ and variable j is set to the value of variable i (step 520). Then, a second test is performed to determine whether or not the variation of entropy $\overline{\Delta S}(r \rightarrow r_i)$ has been calculated for all the possible moves of the sensor (step 525). If the variation of entropy $\overline{\Delta S}(r \rightarrow r_i)$ has not been calculated for all the possible moves of the sensor, the last four steps i.e., steps 505 to 525, are repeated. At the end of the process, variable j indicates the sensor movement that maximizes the variation of entropy $\overline{\Delta S}(r \rightarrow r_i)$.

Search Time

The aim of this section is to derive a lower bound on the expected search time T as a function of the entropy S of the probability distribution for the source location. To that aim, one shall consider the ensemble of probability distributions with fixed entropy S and compute the expected minimal time. In obtaining a lower bound one can relax continuity constraints and allow the searcher to jump, like a grasshopper, from one site to any other. For simplicity, here is considered a spatial lattice with unit mesh size, set by the linear dimension of the searcher which one can choose as a unit of length. Denoting by $p_j$ the probability to find the source at the j-th (in time) point visited, the expected search time reads $$T = \sum_j j p_j.$$

The best possible option is to manifestly visit points in decreasing order of probability and the desired lower bound is obtained by minimization with respect to all possible distributions $p_j$ with fixed entropy S. Thus, one should minimize the following relation, $$T' = \sum_j j p_j + \alpha \left( \sum_j p_j - 1 \right) + \beta^{-1} \left( \sum_j p_j \log p_j + S \right) \quad (18)$$

where $\alpha$ and $\beta$ are the Lagrange multipliers enforcing the normalization of probability and the constraint on the entropy. The probability distribution corresponding to the minimum of the previous relation has a Gibbs form: $p_j \propto \exp(-\beta j)$. If boundaries can be neglected i.e., $S \ll \log N$ where N is the total number of points, the inverse temperature $\beta$ is such that $\beta \gg 1/N$. The relation between the entropy and the search time reads then, $$S = T \log T - (T-1) \log (T-1) \quad (19)$$

In the interesting cases where S and T are both large compared to unity, this reduces to the following relation, $$T = \sum_j j p_j \approx e^{S-1} \equiv \frac{n}{e} \quad (20)$$

In other words, the search time is bounded in terms of the effective number of points $n = e^S$, which is determined by entropy.

Simulation

FIG. 6, comprising FIGS. 6a and 6b, presents the result of a numerical simulation using a model of odor propagation described above, in the absence of wind and in the presence of wind, respectively. Simulations of the search process are realized using a computational model of odor spreading where detectable particles or molecules are emitted by the source at rate R, have a finite lifetime $\tau$, propagate with isotropic effective diffusivity D (which parameterizes the combined effect of turbulent and molecular diffusion) and are advected by a mean current or wind V. This simple model provides a reasonable representation of turbulent advection and mixing. The background concentric lines represent the mean rate of particle or molecule detections and in both cases the rate decays exponentially at large distances. Searcher starts from the points indicated by black upward triangles. Odor detection events along the trajectories are indicated by black circles. Note the long lags where no particles are detected, reflecting the dilute conditions characteristic of odor detection at large distances. In the absence of wind (FIG. 6a), symmetry around the starting point is initially present and the searcher starts spiralling around it (as is observed with sea urchin sperm). Interestingly, in the absence of hits, the radius of the spiral increases in a scale invariant manner, making an approximately Archimedean spiral. As time progresses and information is gathered along the trajectory, the symmetry is broken more and more until the direction towards the source emerges as the preferential one, finally leading thereto. In the presence of wind (FIG. 6b), the search alternates phases of consistent progression upwind with phases of wider crosswind excursion and even downwind movements suggestive of the classical casting and zigzagging patterns observed during bird and moth flights.

FIG. 7 depicts the quantitative characterization of search algorithm. FIG. 7a shows the scaling of the average search time with respect to the initial distance to the source. The mean path travelled by particles or molecule during their lifetime is 50, corresponding to the plateau observed in the figure. The linear scaling at large initial distances favourably compares with the exponential time needed to average out concentration noise. FIG. 7b represents the typical exponential decay of the probability distribution function (PDF) of the search times, indicating that searches are not plagued by strong fluctuations. FIG. 7c is the scaling of the residual search time (time left to locate the source) versus the entropy of the estimated probability distribution for the source location. The quantities are averaged over an ensemble of 1,000 realizations of the search process. Note the exponential dependence of the search time on the entropy of the field, in agreement with theoretical arguments. The exponential dependence indicates that reducing entropy in the estimation of the source location is an effective way to ensure a rapid search process.

Figure 8:
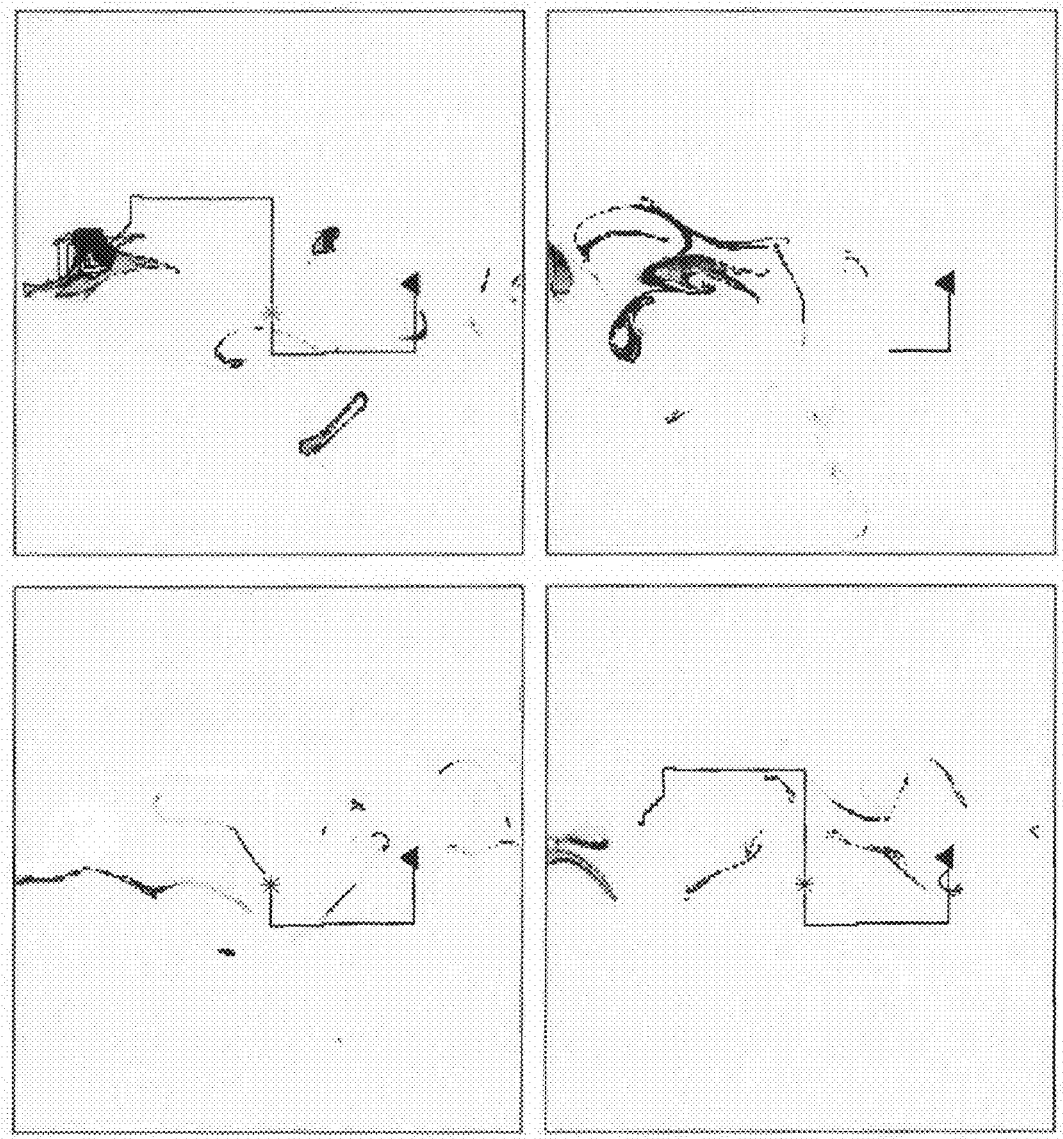
FIG. 8 presents the path generated when localizing a particle source in a simulation utilizing experimental measurements of dye concentration in a turbulent flow.

FIG. 8 presents the path generated in a simulation utilizing experimental measurements of dye concentration in a turbulent flow. "Hits" occur when the searcher encounters concentration above a threshold, which we chose sufficiently high to keep the number of hits low. Simulations indicate that the strategy according to the invention is robust with respect to the searcher's model of the turbulent medium and to fluctuations and inhomogeneities of the medium. Indeed, even the simplistic hypothesis of time-independent odor encounters does not hinder the search. Modelling of the turbulent medium might be further improved by accounting for temporal correlations of odor plume encounter.

Naturally, in order to satisfy local and specific requirements, a person skilled in the art may apply to the solution described above many modifications and alterations all of which, however, are included within the scope of protection of the invention as defined by the following claims.

The invention claimed is:

1. A method implemented by a computer programmed to move a mobile sensor to locate a source of particles, molecules, or fragments of molecules in a search space, the mobile sensor being adapted to detect the presence of such particle, molecule, or fragment of particle, the method comprising:
   determining the particle, molecule, or fragment of molecule diffusion parameters in said search space;
   designing a lattice on said search space;
   determining if at least one particle, molecule, or fragment of molecule is detected by said sensor;
   computing, by a processor of the computer, a probability for each node of said search space lattice to be the source of said particles, molecules, or fragments of molecules according to the determined particle, molecule, or fragment of molecule diffusion parameters and to the detected particles, molecules, or fragments of molecules;
   evaluating a movement of said sensor according to said computed probabilities to locate a source of particles, molecules, or fragments of molecules in a search space; and
   moving said sensor according to the evaluated movement.

2. The method of claim 1 further comprising repeating, until one of said computed probabilities is approximately equal to a predetermined threshold, the steps of
   determining if at least one particle, molecule, or fragment of molecule is detected by said sensor;
   computing a probability for each node of said search space lattice to be the source of said particle, molecule, or fragment of molecule according to the determined particle, molecule, or fragment of molecule diffusion parameters and to the detected particles, molecules or fragments of molecules;
   evaluating a movement of said sensor according to said computed probabilities; and,
   moving said sensor.

3. The method of either claim 1 or claim 2 wherein the rate $R(r|r_0)$ at which particles, molecules, or fragments of molecules are received at point r from the source of said particles, molecules, or fragments of molecules located in $r_0$ is expressed as follow, $$R(r|r_0) = \frac{aR}{|r-r_0|} e^{-\frac{(r-r_0)}{\lambda}} e^{\frac{(y_0-y)V}{2D}}$$

$$\text{with } \lambda = \sqrt{\frac{D\tau}{1+\frac{V^2\tau}{4D}}}$$

the particle, molecule, or fragment of molecule diffusion parameters being,
a that represents the particle, molecule, or fragment of molecule radius;
R that is the particle, molecule, or fragment of molecule emission rate;
$\tau$ that represents the particle, molecule, or fragment of molecule lifetime;
V that is the mean flow presents in said search space;
($y_0$-y) that characterizes the mean flow direction; and,
D that represents the diffusivity of the particles, molecules, or fragments of molecules.

4. The method of claim 1, wherein said probability $P_1(r_0)$ associated to each node of said search space lattice to be the source of said particles, molecules, or fragments of molecules is computed according to the next relation, $$P_t(r_0) = \frac{\exp\left[-\sum_i \int_{v_y} R(r(t')|r_0)dt'\right]\prod_{i=l}^{H} R(r(t_i)|r_0)}{\int \exp\left[-\sum_i \int_{v_y} R(r(t')|x)dt'\right]\prod_{i=l}^{H} R(r(t_i)|x)dx}$$

where $R(r|r_0)$ is the rate at which particles, molecules, or fragments of molecules are received at point r from the source of said particles, molecules, or fragments of molecules located in $r_0$.

5. The method of claim 1, wherein said step of evaluating a movement of said sensor according to said computed probabilities is based upon the entropy of said computed probabilities.

6. The method of claim 5 wherein the movement of said sensor is determined so as to maximize the variation of entropy of said computed probabilities.

7. The method of claim 6 wherein the variation entropy $\overline{\Delta S}(r \to r_j)$ of said computed probabilities is determined according to the following relation, $$\overline{\Delta S}(r \to r_j) = -SP_t(r_j) + (1-P_t(r_j))[\rho_0(r_j)\Delta S_0 + \rho_1(r_j)\Delta S_1 + \ldots + \rho_n(r_n)\Delta S_n]$$

wherein,
$P_t(r_j)$ is the probability at time t that node $r_j$ corresponds to the source of said particles, molecules, or fragments of molecules;
$p_i(r_j)$ denotes the probability that i particle, molecule, or fragment of molecule detections are made at node $r_j$ during 25 a time step $\Delta t$; and,
$\Delta S_i$ denotes the change of entropy between the fields $P_{t+1}(r_0)$ and $P_t(r_o)$.

8. The method of claim 1, wherein at least two different types of particles, molecules, or fragments of molecules are emitted by said source of particles, molecules, or fragments of molecules to be localized, said mobile sensor being adapted to detect each of said at least two different types of particles, molecules, or fragments of molecules, a probability being computed for each of said at least two different types of particles, molecules, or fragments of molecules, for each node of said search space lattice to be the source of said particles, molecules, or fragments of molecules.

9. The method of claim 1, wherein said molecules or fragments of molecules are biological molecules, biological fragments of molecules, proteins, fragments of proteins, or pathogens.

10. The method of claim 1, wherein said particles, molecules, or fragments of molecules 20 characterizes an odorous substance.

11. The method of claim 1, wherein said search space is located within a gaseous environment or within a liquid environment.

12. An apparatus comprising a computer including a computer program to move a mobile sensor to locate a source of particles, molecules, or fragments of molecules in a search space, the mobile sensor being adapted to detect the presence of such particle, molecule, or fragment of particle, the computer program causing the computer to determine the particle, molecule, or fragment of molecule diffusion parameters in said search space;
   design a lattice on said search space;
   determine if at least one particle, molecule, or fragment of molecule is detected by said sensor;

compute, by a processor of the computer, a probability for each node of said search space lattice to be the source of said particles, molecules, or fragments of molecules according to the determined particle, molecule, or fragment of molecule diffusion parameters and to the detected particles, molecules, or fragments of molecules;

evaluate a movement of said sensor according to said computed probabilities; and move the sensor according to the evaluated movement.

13. The apparatus of claim 12, comprising a robot embedding said sensor, said robot being mobile in said search space, wherein-said first robot and said computer exchange data.

14. A non-transitory computer-readable medium storing a computer program that when executed by a computer, causes the computer to move a mobile sensor to locate a source of particles, molecules, or fragments of molecules in a search space, the mobile sensor being adapted to detect the presence of such particle, molecule, or fragment of particle, the computer program comprising instructions to determine the particle, molecule, or fragment of molecule diffusion parameters in said search space;

design a lattice on said search space;

determine if at least one particle, molecule, or fragment of molecule is detected by said sensor;

compute, by a processor of the computer, a probability for each node of said search space lattice to be the source of said particles, molecules, or fragments of molecules according to the determined particle, molecule, or fragment of molecule diffusion parameters and to the detected particles, molecules, or fragments of molecules;

evaluate a movement of said sensor according to said computed probabilities; and move the sensor according to said evaluated movement.

* * * * *